(12) United States Patent
Cheng et al.

(10) Patent No.: US 7,098,364 B2
(45) Date of Patent: Aug. 29, 2006

(54) PHENYLETHANOLAMINE COMPOUNDS AS $\beta_2$-RECEPTOR AGONISTS, AND METHODS OF USE AND PREPARATION THEREOF

(75) Inventors: Maosheng Cheng, Shenyang (CN); Li Pan, Shenyang (CN); Lie Ji, Shenyang (CN); Li Zhang, Shenyang (CN); Jianmin Shen, Shenyang (CN); Guilan Song, Jinzhou (CN); Zhiging Li, Jinzhou (CN)

(73) Assignees: Shenyang Pharmaceutical University, Shenyang (CN); Jinzhou Jiutai Pharmaceutical Co., Ltd., China, Jinzhou (CN)

( * ) Notice: Subject to any disclaimer, the term of this patent is extended or adjusted under 35 U.S.C. 154(b) by 166 days.

(21) Appl. No.: 10/491,028

(22) PCT Filed: Sep. 25, 2002

(86) PCT No.: PCT/CN02/00676

§ 371 (c)(1),
(2), (4) Date: Aug. 16, 2004

(87) PCT Pub. No.: WO03/093219

PCT Pub. Date: Nov. 12, 2003

(65) Prior Publication Data

US 2004/0266867 A1 Dec. 30, 2004

(30) Foreign Application Priority Data

Sep. 30, 2001 (CN) .............................. 01 1 28234

(51) Int. Cl.
*C07C 215/20* (2006.01)
*A61K 31/135* (2006.01)

(52) U.S. Cl. ...................................... 564/355; 514/653
(58) Field of Classification Search ................ 564/355
See application file for complete search history.

(56) References Cited

OTHER PUBLICATIONS

Database CAPLUS on STN, Acc. No. 1997:132857, Brodfuehrer et al., Organic Process Research & Development (1997), 1(2), p. 176-178 (abstract).*
Database CAPLUS on STN, Acc. No. 2001:86611, Boger et al., Journal of the American Chemical Society (2001), 123(9), p. 1862-1871 (abstract).*

* cited by examiner

*Primary Examiner*—Brian Davis
(74) *Attorney, Agent, or Firm*—Wilson Sonsini Goodrich & Rosati

(57) ABSTRACT

The invention provides compounds of formula (I) and pharmaceutically acceptable salts thereof, wherein $R_1$ is H, chlorine, or bromine; $R_2$ is electron attractive groups selected from the group consisting of $CF_3$, CN, fluorine, $CH_3SO_3$, $CF_3SO_3$, and $NO_2$; $R_3$ is linear or branched alkyl having 1 to 10 carbon atoms, linear or branched alkoxyalkyl having 2 to 10 carbon atoms, aliphatic alcohol having 1 to 10 carbon atoms, or cycloalkyl having 3 to 6 carbon atoms. The invention also relates to methods for preparing the said compounds and the composition comprising the same. The compounds of the present invention have the effect of $\beta_2$-receptor agonist and can be used for the treatment of asthma and bronchitis

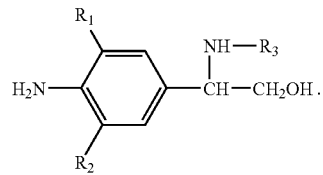

18 Claims, No Drawings

PHENYLETHANOLAMINE COMPOUNDS AS $\beta_2$-RECEPTOR AGONISTS, AND METHODS OF USE AND PREPARATION THEREOF This application is a 371 of PCT/CN02/00676 filed Sep. 12, 2002.

TECHNICAL FIELD

The present invention relates to new compounds for the treatment of asthma and bronchitis, in particularly, new phenylethanol-amines compounds as $\beta_2$-receptor agonist.

BACKGROUND ART

The asthma and bronchitis are common diseases. In most case, their therapies are through using antibiotics, which are not very effective and have some side effect in longer usage. $\beta_2$-Receptor agonists are well known as anti-asthma agents. However, these agents are still deficient in effects and physical and chemical properties.

DISCLOSURE OF THE INVENTION

The invention relates to phenylethanol-amines compounds of formula (I) and pharmaceutically acceptable salts thereof:

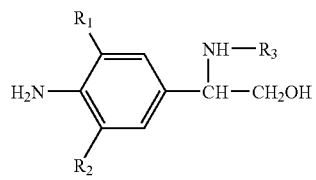

(I)

wherein
$R_1$ is H, chlorine, or bromine;
$R_2$ is electron attractive groups selected from the group consisting of $CF_3$, CN, fluorine, $CH_3SO_3$, $CF_3SO_3$, and $NO_2$;
$R_3$ is linear or branched alkyl having 1 to 10 carbon atoms, linear or branched alkoxyalkyl having 2 to 10 carbon atoms, aliphatic alcohol having 1 to 10 carbon atoms, or cycloalkyl having 3 to 6 carbon atoms.

According to one embodiment of the invention, $R_2$ is preferably $CF_3$ or CN.

According to another embodiment of the invention, $R_3$ is linear or branched alkyl having 1 to 6 carbon atoms, linear or branched alkoxy having 2 to 6 carbon atoms, aliphatic alcohol having 1 to 6 carbon atoms, or cycloalkyl having 3 to 6 carbon atoms.

The term "pharmaceutically acceptable salt" used in herein refers to conventional acid-addition salts or base-addition salts which retain the biological effectiveness and properties of the compounds of formula (I) and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, phosphoric acid and nitric acid, those derived from organic acids such as acetic acid, tartaric acid, salicylic acid, methanelsulfonic acid, butanedioic acid, citric acid, malic acid, lactic acid, fumaric acid, and the like. Sample base-addition salts include those derived from potassium, sodium, ammonium.

In particularly, the pharmaceutically acceptable salts of the compounds of formula (I) are preferably hydrochloride or hydrobromide.

The present invention also provides a method for preparing the compounds of formula (I), comprising
reacting the free base of formula (III) or pharmaceutically acceptable salts thereof

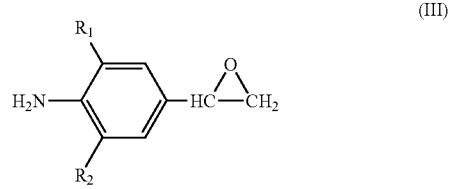

(III)

wherein $R_1$ and $R_2$ are as defined above,
with the compounds of formula (IV)

$H_2NR_3$ (IV)

wherein $R_3$ is as defined above.

The compounds of formula (I) according to the present invention can be prepared by the above methods. The reaction of compounds of formula (III) and the compounds of formula (IV) is carried out in the anhydrous condition, for example in the solvent of alcohols, such as anhydrous ethanol or aromatic hydrocarbons, such as toluene at a temperature of refluxing temperature of solvent for 10–15 h. The yield is 20–30%.

In the present invention, compounds of formula (III) can be prepared by the following scheme:

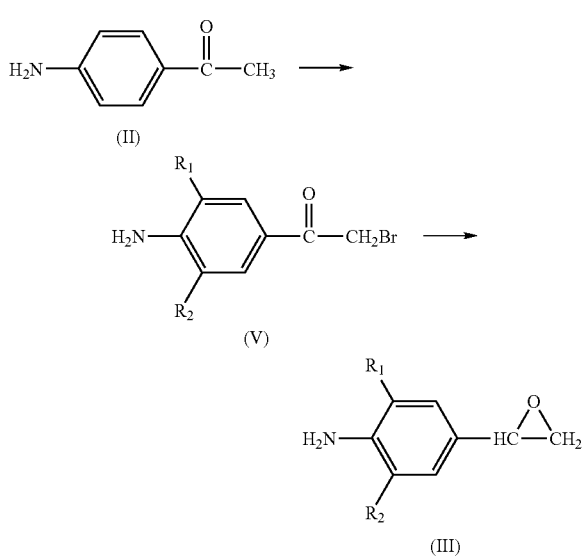

wherein the p-amino acetophenone can be used as free base of formula (II) or pharmaceutically acceptable salts thereof.

The method for preparing compounds of formula (V) from compounds of formula (II) is well known to those skilled in the art (for example, Kurger G, Keck J. and Pieper H. Synthesis of amino-Halogen-Substituted Phenyl-amino-ethanols. Arzneim Forsch./Drug res. 34(11), Nr. Ba, 1984: 1612–1624, which is incorporated herein by reference).

The compounds of formula (III) are prepared from the compounds of formula (V) by reduction with potassium borohydride in methanol and water at room temperature for 5 h.

The present invention also provides a pharmaceutical composition comprising at least one compound of formula (I) or pharmaceutically acceptable salts thereof. The pharmaceutical composition according to the present invention further comprises one or more pharmaceutically acceptable excipients and other active ingredients.

The "pharmaceutically acceptable excipients" means an excipient that is useful in pharmaceutical fields that is generally safe, non-toxic and neither biologically nor undesirable effect. These excipients also include lactose, starch, water, alcohol, and the like.

The pharmaceutical composition according to the present invention can also include propellents, antiseptics, solubilizing agents, stabilizing agents, moistening agents, emulsifiers, sweeting agents, colorants, flavoring agents, salts for adjusting osmotic pressure, buffer, coating agents, antioxitants, and the like. The pharmaceutical composition according to the present invention can also comprise other therapeutically valuable substance, for example other active ingredients other than the compound of formula (I).

The pharmaceutical composition according to the present invention can be prepared into tablets, capsules, solutions, sprays, injections, and the like. It can be administrated by oral, parenteral, spraying, inhaling through oral or nasal cavity or other forms.

The compounds of the present invention have the effect of $\beta_2$-receptor agonist and can be used for the treatment of asthma and bronchitis. The present invention relates to use of the compound of formula (I) in the preparation of medicaments having effect of $\beta_2$-receptor agonist. The present invention also relates to use of the compound of formula (I) in the preparation of medicaments for the treatment of asthma and bronchitis.

The compounds of the present invention can be administrated in a therapeutically effective amount. The "a therapeutically effective amount" means an amount that effectively prevent, alleviate, improve the diseases conditions. The "a therapeutically effective amount" can be determined by those skilled in the art.

The therapeutically effective amount or dose may be changed in a broad scope, and may be adjusted according to requirement of individual case. Typically, for adults with about 70 Kg weight, preferably the dose is about 50 μg-10 mg/day when administrated in oral or parenteral form. When required, the upper limit and low limit of dose can be exceeded. The daily dose can be administrated alone or divided in several times.

The compounds according to the present invention can be prepared according to above scheme by using known synthesis methods. The following examples illustrate preferable synthesis method of these compounds.

EXAMPLE 1

2-(4-amino-3-chloro-5-trifluoromethyl-phenyl)-2-tert-butylamino-ethanol hydrochloride a. Preparation of 4-amino-3-chloro-5-trifluoromethyl-benzoyl chloride 13 g (0.0543 mol) of 4-amino-3-chloro-5-trifluoromethyl-benzoic acid was added to 32.5 ml of thionyl chloride. The suspension was heated until the crystals have dissolved, then refluxing was continued for another 2 h. After cooling to room temperature, the remaining thionyl chloride was evaporated under reduced pressure, thus obtained crude 3-chloro-4-amino-5-trifluoromethyl-benzoyl chloride, which was dissolved in chloroform at heating. Filtered with heating and evaporated under reduced pressure to remove chloroform, obtained the subject product. Yield: 80–90%, melting point: 110–115° C.

b. 4-amino-3-chloro-5-trifluoromethyl-acetophenone

To reaction flask 1.31 g (0.0535 mol) of magnesium turnings, 1.6 ml of absolute ethanol and 0.12 ml of carbon tetrachloride were added at room temperature. Heated, 14.6 ml of absolute tetrahydrofuran were added at such a rate that refluxing was maintained. Under continued refluxing and stirring a mixture of 8.1 ml(0.0534 mol) of diethyl malonate, 4.8 ml of absolute ethanol and 5.6 ml of tetrahydrofuran was added dropwise over 1 h, followed by reflux for 2 h. 13.1 g (0.05.1 mol) 4-amino-3-chloro-5-trifluoromethyl-benzoyl chloride was dissolved in 43.5 ml tetrahydrofuran, and was added dropwise to above reaction solution over 0.5 h. After added, continue to reflux for 2 h. After cooling to room temperature, 2N sulfuric acid were dropped to adjust pH to 2. Organic phase was separated, evaporated under reduced pressure to obtain oil. A mixture of 45.8 ml of glacial acetic acid, 30.6 ml of water and 5.7 ml of concentrated sulfuric acid was added, refluxed. with heating for 5 h. Evaporated under reduced pressure to remove solvent. The solid obtained was dissolved in chloroform. Ice water was added, and pH was adjusted to 8 with 50% solution of sodium hydroxide. The chloroform phase was separated, washed with water, dried, filtered, and evaporated under reduced pressure to remove chloroform. The crude was obtained. Yield: 75–85%, melting point: 120–130° C.

c. 4-amino-3-chloro-5-trifluoromethyl-alpha-bromo-acetophenone 8.5 g (0.0358 mol) of 4-amino-3-chloro-5-trifluoromethyl-acetophenone was dissolved in 85 ml of glacial acetic acid. At 45–50° C. a solution of 2 ml (0.0394 mol) of bromine in 17 ml of glacial acetic acid was added dropwise. Heating was continued for a further 30 min. The acetic acid was evaporated, the oily residue was taken up in 100 ml of ethyl acetate, washed with sodium hydrogen carbonate solution and water respectively, dried and evaporated under reduced pressure to obtain crude product, which was recrystallized in mixed solvents of toluene and cyclohexane to obtained purified crystals. Yield 50–60%; melting point 113–115° C.

d. 5.6 g (0.01769 mol) 4-amino-3-chloro-5-trifluoromethyl-alpha-bromo-acetophenone was dissolved in 56 ml of methanol and 4.9 ml of water was added. At room temperature 0.96 g (0.1769 mol) of potassium borohydride were added in small portions and the reaction mixture was stirred for 5 h, then cooled to 0° C. with ice-water and carefully acidified to a pH=2 with 2N hydrochloric acid. Evaporated under reduced pressure and the remaining mass was dissolved in 11.2 ml of water and extracted with chloroform (3×10 ml). The organic phase was washed with water to neutrality, dried over anhydrous $MgSO_4$ and evaporated to dryness, to give (4-amino-3-chloro-5-trifluoromethyl-phenyl)-ethylene oxide as oil. Yield 85–95%; $^1$H-NMR (DMSO-$d_6$) δ: 2.88(2H, d), 3.89(1H, t), 7.08(1H, s), 7.24 (1H, s).

e. 5.2 g (0.022 mol) of (4-amino-3-chloro-5-trifluoromethyl-phenyl)-ethylene oxide was dissolved in 26 ml of anhydrous ethanol and treated with 5.1 ml (0.049 mol) of tert-butylamine. The mixture was refluxed for 13 h, and then evaporated. The residue was extracted with 2N hydrochloric acid for several times. Aqueous layers were combined and extracted with toluene and treated with activated carbon.

The pH was adjusted to 10 with 20% sodium hydroxide solution. The precipitate was collected by filtration, 2-(4-amino-3-chloro-5-trifluoromethylphenyl)-2-tert-butylaminoethanol was obtained. Yield 20–30%; melting point 85–90° C.

f. 1.0 g of 2-(4-amino-3-chloro-5-trifluoromethylphenyl)-2-tert-butylaminoethanol was dissolved in 20 ml of diethyl ether and filtered. Saturated solution of hydrogen chloride in isopropanol was added dropwise and acidified to pH=2. The precipitate was collected by filtration, washed with anhydrous ether, and dried to give crude 2-(4-amino-3-chloro-5-trifluoromethyl-phenyl)-2-tert-butylaminoethanol hydrochloride. The crude product was dissolved in absolute ethanol at a ratio of 1:5 w/v. Filtered, anhydrous ether was added dropwise until small amount of crystals was precipitated. Lyophilized and filtered to give 2-(4-amino-3-chloro-5-trifluoromethyl-phenyl)-2-tert-butylaminoethanol hydrochloride. Yield 80–90%; melting point 205–206° C. (dec). $^1$H-NMR (DMSO-$d_6$) δ:1.24 (9H, s), 3.77(2H, d), 4.42–4.44 (1H, m), 7.72(1H, s), 7.87(1H, s).

EXAMPLE 2 a. Preparation of 3-iodo-4-amino-acetophenone 40 g of 4-aminoacetophenone, 150 g of iodine and 59.4 g of calcium carbonate were dissolved in 1.2 L methanol and 230 mL water and stirred at room temperature for 70–80 h. Sodium thiosulfate was added, stirred, filtered, and evaporated. Aqueous layer was extracted with chloroform and washed with sodium thiosulfate and water in turn. Evaporated to give product as red brown oil. Yield 60–90%.

b. Preparation of 3-cyano-4-amino-acetophenone

The 3-iodo-4-amino-acetophenone as prepared above was dissolved 95 ml of DMF and 20.9 g CuCN was added. Stirred under reflux for 6 h and cooled down to 100° C. The reaction mixture was poured into 2 L of water, and cooled. The precipitate was filtered off, air dried and extracted with THF. Evaporated, washed with ethanol, filtered, and dried to give product as yellow crystal. Yield 56.9%; melting point 150–152° C.

c. Preparation of 3-cyano-4-amino-alpha-bromo-acetophenone

The mixture of 20.0 g of 3-cyano-4-amino-acetophenone and 54.28 g of copper bromide in 300 ml of THF was refluxed for 4 h, cooled, and filtered at room temperature. The filtrate was distilled in vacuo to remove THF. The residue was washed with small amount of ethanol to give title product as yellow solid. Yield 94.8%; melting point 160–161° C.(decomp.).

d. Preparation of 3-cyano-4-amino-5-bromo-acetophenone 2.0 g of 3-cyano-4-amino-alpha-bromo-acetophenone was dissolved in 40 ml of glacial acetic acid. Stirred and heated to 35° C. 1.48 g of NBS was added to the solution in small portions and continue to stir for 1 h at the same temperature, then poured into 120 mL of water. The precipitate was filtered off and dried to give title product as yellow solid. Yield 82.8%; melting point 165–167° C.

EXAMPLE 3

2-(4-amino-3-chloro-5-trifluoromethyl-phenyl)-2-isopropylamino-ethanol hydrochloride was prepared in a method analogous to Example 1.

$^1$H-NMR(DMSO-$d_6$) δ: 1.08(6H, d), 2.84–2.86 (1H, m), 3.80(2H, d), 4.37–4.39(1H, m), 7.70 (1H, s), 7.80(1H, s).

EXAMPLE 4

2-(4-amino-3-chloro-5-trifluoromethyl-phenyl)-2-cyclopentylamino-ethanol hydrochloride was prepared in a method analogous to Example 1.

$^1$H-NMR (DMSO-$d_6$) δ: 1.62–1.64 (4H, m), 1.65–1.69 (4H, m), 2.64–2.68(1H, m), 3.79(2H, d), 4.43–4.46(1H, m), 7.62(1H, s), 7.77(1H, s).

EXAMPLE 5

2-(4-amino-3-chloro-5-trifluoromethyl-phenyl)-2-cyclohexylamino-ethanol hydrochloride was prepared in a method analogous to Example 1.

$^1$H-NMR (DMSO-$d_6$) δ: 1.29–1.31 (6H, m), 1.40–1.44 (4H, m), 2.78–2.81(1H, m), 3.74(2H, d), 4.39–4.41(1H, m), 7.62(1H, s), 7.89(1H, s).

EXAMPLE 6

2-(4-amino-3-bromo-5-trifluoromethyl-phenyl)-2-tert-butylamino-ethanol hydrochloride was prepared in a method analogous to Example 1.

$^1$H-NMR (DMSO-$d_6$) δ: 1.25(9H, s), 3.76(2H, d), 4.40–4.42(1H, m), 7.62(1H, s), 7.78(1H, s).

EXAMPLE 7

2-(4-amino-3-bromo-5-trifluoromethyl-phenyl)-2-isopropylamino-ethanol hydrochloride was prepared in a method analogous to Example 1. $^1$H-NMR(DMSO-$d_6$) δ: 1.08(6H, d), 2.83–2.86(1H, m), 3.82(2H, d), 4.32–4.34(1H, m), 7.76 (1H, s), 7.90(1H, s).

EXAMPLE 8

2-(4-amino-3-bromo-5-trifluoromethyl-phenyl)-2-cyclopropylamino-ethanol hydrochloride was prepared in a method analogous to Example 1.

$^1$H-NMR (DMSO-$d_6$) δ: 0.80–0.86(4H, m), 1.60–1.63 (1H, m), 3.82(2H, d), 4.40–4.42(1H, m), 7.69(1H, s), 7.88 (1H, s).

EXAMPLE 9

2-(4-amino-3-bromo-5-trifluoromethyl-phenyl)-2-cyclobutylamino-ethanol hydrochloride was prepared in a method analogous to Example 1.

$^1$H-NMR (DMSO-$d_6$) δ: 2.00–2.05(2H, m), 2.14–2.18 (4H, m), 3.13–3.16(1H, m), 3.79(2H, d), 4.40–4.42(1H, m), 7.68(1H, s), 7.78(1H, s).

EXAMPLE 10

2-(4-amino-3-chloro-5-cyanophenyl)-2-tert-butylamino-ethanol hydrochloride was prepared in a method analogous to Example 1.

$^1$H-NMR (DMSO-$d_6$) δ: 1.26(9H, s), 3.75(2H, d), 4.39–4.41(1H, m), 7.79(1H, s), 7.92(1H, s).

EXAMPLE 11

2-(4-amino-3-chloro-5-cyanophenyl)-2-isopropylamino-ethanol hydrochloride was prepared in a method analogous to Example 1.

$^1$H-NMR(DMSO-$d_6$) δ: 1.08(6H, d), 2.82–2.86(1H, m), 3.78(2H, d), 4.38–4.40(1H, m), 7.75 (1H, s), 7.89(1H, s).

EXAMPLE 12

2-(4-amino-3-chloro-5-cyanophenyl)-2-cyclobutylamino-ethanol hydrochloride was prepared in a method analogous to Example 1.

$^1$H-NMR (DMSO-d$_6$) δ: 2.05–2.07(2H, m), 2.11–2.16 (4H, m), 3.10–3.13(1H, m), 3.77(2H, d), 4.41–4.43(1H, m), 7.78(1H, s), 7.88(1H, s).

EXAMPLE 13

2-(4-amino-3-chloro-5-cyanophenyl)-2-cyclopentylamino-ethanol hydrochloride was prepared in a method analogous to Example 1.

$^1$H-NMR (DMSO-d$_6$) δ: 1.62–1.65(4H, m), 1.67–1.69 (4H, m), 2.53–2.57(1H, m), 3.75(2H, d), 4.44–4.46(1H, m), 7.72(1H, s), 7.97(1H, s).

EXAMPLE 14

2-(4-amino-3-bromo-5-cyanophenyl)-2-tert-butylamino-ethanol hydrochloride was prepared in a method analogous to Example 1.

$^1$H-NMR (DMSO-d$_6$) δ: 1.24(9H, s), 3.72(2H, d), 4.36–4.38(1H, m), 7.75(1H, s), 7.95(1H, s).

EXAMPLE 15

2-(4-amino-3-bromo-5-cyanophenyl)-2-isopropylamino-ethanol hydrochloride was prepared in a method analogous to Example 1.

$^1$H-NMR(DMSO-d$_6$) δ: 1.06(6H, d), 2.84–2.87(1H, m), 3.75(2H, d), 4.40–4.43(1H, m), 7.79 (1H, s), 7.89(1H, s).

EXAMPLE 16

2-(4-amino-3-bromo-5-cyanophenyl)-2-cyclobutylamino-ethanol hydrochloride was prepared in a method analogous to Example 1.

$^1$H-NMR (DMSO-d$_6$) δ: 2.10–2.13(2H, m), 2.14–2.17 (4H, m), 3.13–3.16(1H, m), 3.76(2H, d), 4.40–4.43(1H, m), 7.78(1H, s), 7.92(1H, s).

EXAMPLE 17

2-(4-amino-3-bromo-5-cyanophenyl)-2-cyclopentylamino-ethanol hydrochloride was prepared in a method analogous to Example 1.

$^1$H-NMR (DMSO-d$_6$) δ: 1.60–1.63 (4H, m), 1.65–1.68 (4H, m), 2.51–2.53(1H, m), 3.73(2H, d), 4.42–4.45(1H, m), 7.78(1H, s), 7.87(1H, s).

EXAMPLE 18

2-(4-amino-3-bromo-5-cyanophenyl)-2-cyclohexylamino-ethanol hydrochloride was prepared in a method analogous to Example 1.

$^1$H-NMR (DMSO-d$_6$) δ: 1.30–1.35 (6H, m), 1.45–1.49 (4H, m), 2.80–2.86(1H, m), 3.76(2H, d), 4.38–4.43(1H, m), 7.76(1H, s), 7.89(1H, s).

EXAMPLE 19

2-(4-amino-3-cyano-phenyl)-2-tert-butylamino-ethanol hydrochloride was prepared in a method analogous to Example 1.

$^1$H-NMR (DMSO-d$_6$) δ: 1.25(9H, s), 3.72(2H, d), 4.41–4.42(1H, m), 7.62 (1H, d), 7.70(1H, s), 7.85(1H, d).

EXAMPLE 20

2-(4-amino-3-cyano-phenyl)-2-isopropylamino-ethanol hydrochloride was prepared in a method analogous to Example 1.

$^1$H-NMR(DMSO-d$_6$) δ: 1.08(6H, d), 2.77–2.79(1H, m), 3.79(2H, d), 4.43–4.46(1H, m), 7.69 (1H, d), 7.72(1H, s), 7.80(1H, d).

EXAMPLE 21

2-(4-amino-3-cyano-phenyl)-2-cyclobutylamino-ethanol hydrochloride was prepared in a method analogous to Example 1.

$^1$H-NMR (DMSO-d$_6$) δ: 2.09–2.11(2H, m), 2.13–2.19 (4H, m), 3.18–3.21(1H, m), 3.75(2H, d), 4.38–4.31(1H, m), 7.68(1H, d), 7.75(1H, s), 7.82(1H, d).

EXAMPLE 22

2-(4-amino-3-cyano-phenyl)-2-cyclopentylamino-ethanol hydrochloride was prepared in a method analogous to Example 1.

$^1$H-NMR (DMSO-d$_6$) δ: 1.62–1.65 (4H, m), 1.68–1.72 (4H, m), 2.53–2.56(1H, m), 3.70(2H, d), 4.48–4.51(1H, m), 7.68(1H, d), 7.73(1H, s), 7.87(1H, d).

EXAMPLE 23

2-(4-amino-3-cyano-phenyl)-2-cyclopropylaamino-ethanol hydrochloride was prepared in a method analogous to Example 1.

$^1$H-NMR (DMSO-d$_6$) δ: 0.89–0.93(4H, m), 1.23–1.26 (1H, m), 3.75(2H, d), 4.38–4.42(1H, m), 7.69(1H, d), 7.76 (1H, s), 7.80(1H, d).

EXAMPLE 24

2-(4-amino-3-chloro-5-trifluoromethyl-phenyl)-2-(2-methyl-3-hydroxyl-2-propylamino)-ethanol hydrochloride was prepared in a method analogous to Example 1.

$^1$H-NMR (DMSO-d$_6$) δ: 1.18(6H, s), 3.61(2H, s), 3.94 (2H, d), 4.20–4.23(1H, m), 6.95(1H, s), 7.11(1H, s).

EXAMPLE 25

2-(4-amino-3-bromo-5-trifluoromethyl-phenyl)-2-(2-methyl-3-hydroxyl-2-propylamino)-ethanol hydrochloride was prepared in a method analogous to Example 1.

$^1$H-NMR (DMSO-d$_6$) δ: 1.18(6H, s), 3.68(2H, s), 3.94 (2H, d), 4.18–4.21(1H, m), 7.06(1H, s), 7.08(1H, s).

EXAMPLE 26

2-(4-amino-3-chloro-5-cyanophenyl)-2-(2-methyl-3-hydroxyl-2-propylamino)-ethanol hydrochloride was prepared in a method analogous to Example 1.

$^1$H-NMR (DMSO-d$_6$) δ: 1.17(6H, s), 3.62(2H, s), 4.01 (2H, d), 4.16–4.18(1H, m), 7.09(1H, s), 7.20(1H, s).

EXAMPLE 27

2-(4-amino-3-bromo-5-cyanophenyl)-2-(2-methyl-3-hydroxyl-2-propylamino)-ethanol hydrochloride was prepared in a method analogous to Example 1.

$^1$H-NMR (DMSO-d$_6$) δ: 1.19(6H, s), 3.60(2H, s), 3.98 (2H, d), 4.06–4.09(1H, m), 7.09(1H, s), 7.32(1H, s).

EXAMPLE 28

2-(4-amino-3-cyano-phenyl)-2-(2-methyl-3-hydroxyl-2-propylamino)-ethanol hydrochloride was prepared in a method analogous to Example 1.

$^1$H-NMR (DMSO-d$_6$) δ: 1.20(6H, s), 3.56(2H, s), 3.98 (2H, d), 4.10–4.13(1H, m), 6.60(1H, d), 7.13(1H, s), 7.20 (1H, d).

EXAMPLE 29

2-(4-amino-3-chloro-5-trifluoromethyl-phenyl)-2-tert-butylamino-ethanol hydrobromide 1.0 g of 2-(3-chloro-4-amino-5-trifluoromethyl-phenyl)-2-tert-butylaminoethanol was dissolved in 20 ml of anhydrous diethyl ether and the solution was acidified to pH=2 by adding dropwise a solution of hydrobromic acid in isopropanol with stirring. The precipitate was collected by filtration, washed with small amount of anhydrous diethyl ether, dried to give crude 2-(4-amino-3-chloro-5-trifluoromethyl-phenyl)-2-tert-butylamino-ethanol hydrobromide. The crude product was dissolved in absolute ethanol at a ratio of 1:5 w/v. Filtered and anhydrous diethyl ether was added dropwise until small amount of crystals was precipitated. Lyophilized and filtered to give 2-(4-amino-3-chloro-5-trifluoromethyl-phenyl)-2-tert-butylamino-ethanol hydrobromide. Yield 80–90%; melting point 208–210° C. (dec.) $^1$H-NMR (DMSO-d$_6$) δ: 1.24(9H, s), 3.79(2H, d), 4.46–4.51(1H, m), 7.72(1H, s), 7.89(1H, s).

EXAMPLE 30

2-(4-amino-3-chloro-5-trifluoromethyl-phenyl)-2-(3-ethoxyl-2-propylamino)-ethanol hydrochloride was prepared in a method analogous to Example 1.

$^1$H-NMR (DMSO-d$_6$) δ:1.08 (3H, t), 1.84–1.98(2H, m), 2.71–2.84(2H, m), 3.32–3.39(4H, m), 3.82(2H, d), 4.25–4.27(1H, m), 5.60(1H, s), 5.90(2H, s), 7.69(1H, s), 7.87(1H, s), 9.39(2H, s).

EXAMPLE 31

2-(4-amino-3-bromo-5-trifluoromethyl-phenyl)-2-(3-ethoxyl-2-propylamino)-ethanol hydrochloride was prepared in a method analogous to Example 1.

$^1$H-NMR (DMSO-d$_6$) δ:1.09 (3H, t), 1.92–1.98(2H, m), 2.73–2.78(2H, m), 3.30–3.36(4H, m), 3.79(2H, d), 4.22–4.26(1H, m), 5.68(1H, s), 5.89(2H, s), 7.71(1H, s), 7.86(1H, s), 9.38(2H, s).

EXPERIMENT EXAMPLE

The antagonistic effects of bronchoconstrtriction induced by histamine of the compounds of the present invention were evaluated by isolated guinea pig trachea strips.

Apparatus: polygrapher recorder, strain gauge transducer

Conditions: Krebs-Hensleit solution; gas mixture(95% O$_2$, 5% CO$_2$); Paper speed: 4 mm/min; 37° C.

Animals: guinea pigs (Harley, purchased from the Experimental Animal Center of China Medical University) of either sex weighting 350–500 g were used.

Reagent: Histamines phosphate solution($10^{-6}$–$10^{-4}$M)

Sample: Depending on their potencies, the compounds were tested at the concentration of $10^{-6}$ or $3 \times 10^{-4}$M.

Method: Guinea pigs were sacrificed and the trachea strips(2 cm×3 mm) were prepared; the preparation was then mounted under a testing tension of 2 g in an organ bath containing 10 mL Kebs-Hensleits solution at 37° C. and superfused with the gas mixture mentioned above and the preparation was allowed to equilibrate for 2 h before the addition of histamine. When the tension of trachea strips reached 50% of the maximum contraction, the tested compounds was added to bath, and the antagonistic effect (represented as relaxing rate) was calculated as below:

Relaxing rate=(Contraction intensity after histamine addition-Contraction intensity after tested compounds addition)/ Contraction intensity after tested compounds addition× 100%

The relaxing rate of each compound was presented in table 1.

TABLE 1

Antagonistic effect of the active compounds on bronchus contracting induced by histamine

| Structure of the compounds | Relaxing rate (%) |
| --- | --- |
| Cl, H$_2$N—, F$_3$C substituted phenyl with HN—CH(CH$_3$)$_2$, CH—CH$_2$—OH ·HCl | 52.5 |
| Cl, H$_2$N—, F$_3$C substituted phenyl with HN—CH(CH$_3$)$_3$, CH—CH$_2$—OH ·HCl | 181.2 |
| Cl, H$_2$N—, NC substituted phenyl with HN—CH(CH$_3$)$_2$, CH—CH$_2$—OH ·HCl | 69.2 |
| Cl, H$_2$N—, F$_3$C substituted phenyl with HN-cyclohexyl, CH—CH$_2$—OH ·HCl | 2.1 |

TABLE 1-continued

Antagonistic effect of the active compounds on bronchus contracting induced by histamine

| Structure of the compounds | Relaxing rate (%) |
|---|---|
| 3-Br, 4-NH₂, 5-CF₃ phenyl -CH(NHCH(CH₃)₂)-CH₂-OH · HCl | 65.1 |
| 3-Br, 4-NH₂, 5-CF₃ phenyl -CH(NHC(CH₃)₃)-CH₂-OH · HCl | 59.3 |
| 3-Br, 4-NH₂, 5-CF₃ phenyl -CH(NH-cyclopropyl)-CH₂-OH · HCl | 10.2 |
| 3-Cl, 4-NH₂, 5-CN phenyl -CH(NH-cyclobutyl)-CH₂-OH · HCl | 36.7 |
| 3-Br, 4-NH₂, 5-CN phenyl -CH(NHCH(CH₃)₂)-CH₂-OH · HCl | 77.6 |
| 3-Br, 4-NH₂, 5-CN phenyl -CH(NHC(CH₃)₃)-CH₂-OH · HCl | 73.1 |
| 3-Br, 4-NH₂, 5-CN phenyl -CH(NH-cyclobutyl)-CH₂-OH · HCl | 30.8 |
| 4-NH₂, 3-CN phenyl -CH(NH-cyclobutyl)-CH₂-OH · HCl | 18.9 |
| 3-Br, 4-NH₂, 5-CN phenyl -CH(NH-cyclohexyl)-CH₂-OH · HCl | 3.2 |
| 4-NH₂, 3-CN phenyl -CH(NHCH(CH₃)₂)-CH₂-OH · HCl | 60.3 |
| 3-Br, 4-NH₂, 5-CF₃ phenyl -CH(NH-cyclobutyl)-CH₂-OH · HCl | 12.9 |
| 3-Cl, 4-NH₂, 5-CN phenyl -CH(NHCH(CH₃)₂)-CH₂-OH · HCl | 70.5 |
| 3-Cl, 4-NH₂, 5-CF₃ phenyl -CH(NHC(CH₃)₂CH₂OH)-CH₂OH · HCl | 85.1 |
| 3-Br, 4-NH₂, 5-CF₃ phenyl -CH(NHC(CH₃)₂CH₂OH)-CH₂OH · HCl | 128.2 |

TABLE 1-continued

Antagonistic effect of the active compounds on bronchus contracting induced by histamine

| Structure of the compounds | Relaxing rate (%) |
|---|---|
| 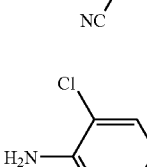 | 15.3 |
| 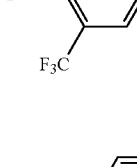 | 8.6 |
| 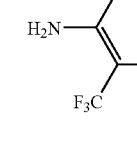 | 55.6 |
| 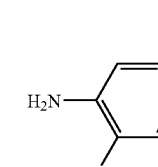 | 15.7 |
| 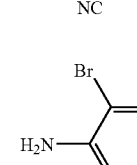 | 89.6 |
| 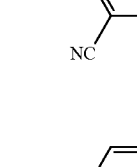 | 65.3 |
| 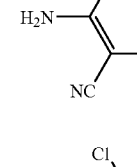 | 165.9 |

TABLE 1-continued

Antagonistic effect of the active compounds on bronchus contracting induced by histamine

| Structure of the compounds | Relaxing rate (%) |
|---|---|
| 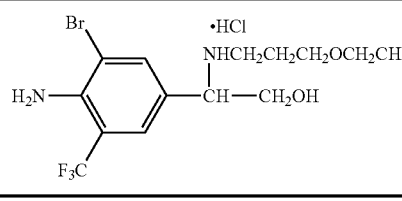 | 9.0 |

The above results showed that the compounds of the present invention have an alleviation effect on trachea spasm induced by histamine.

What is claimed is:

1. A compound of formula (I)

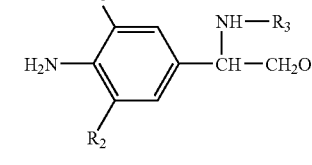

wherein:
$R_1$ is H, chlorine, bromine, iodine, or cyano;
$R_2$ is an electron attractive group selected from the group consisting of $CF_3$, CN, fluorine, $COSO_3H$, $CF_3SO_3$, and $NO_2$; and
$R_3$ is linear or branched alkyl having 1 to 10 carbon atoms, linear or branched alkoxyalkyl having 2 to 10 carbon atoms, aliphatic alcohol having 1 to 10 carbon atoms, or cycloalkyl having 3 to 6 carbon atoms;
or a pharmaceutically acceptable salt thereof.

2. The compound according to claim 1, wherein $R_2$ is $CF_3$ or CN.

3. The compound according to claim 1, wherein $R_3$ is linear or branched alkyl having 1 to 6 carbon atoms, linear or branched alkoxy having 2 to 6 carbon atoms, aliphatic alcohol having 1 to 6 carbon atoms, or cycloalkyl having 3 to 6 carbon atoms.

4. The compound according to claim 1, wherein the pharmaceutically acceptable salt of the compound of formula (I) is a hydrochloride or hydrobromide salt.

5. A method for preparing the compound of claim 1, comprising
reacting the free alkali of formula (III) or a pharmaceutically acceptable salt thereof

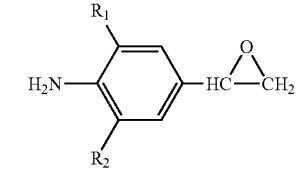

wherein $R_1$ and $R_2$ are as defined in claim 1, with a compound of formula (IV)

$$H_2NR_3 \quad (IV)$$

wherein $R_3$ is as defined in claim 1.

6. The method according to claim 5, wherein the reaction of compounds of formula (III) and the compounds of formula (IV) is carried out under an anhydrous condition; the reacting solvent is an alcohol or an aromatic hydrocarbon; the reacting temperature is the refluxing temperature of the reacting solvent; the reacting period is 10–15 hr; and the yield is 20–30%.

7. A pharmaceutical composition comprising the compound according to any one of claims 1–4 and a pharmaceutically acceptable excipient.

8. A method of stimulating $\beta_2$-Receptor in a subject in need thereof, comprising:
administering to the subject a compound of formula (I)

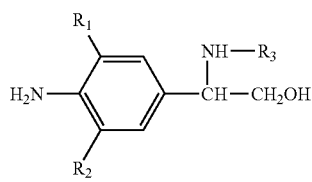

wherein:
$R_1$ is H, chlorine, bromine, iodine, or cyano;
$R_2$ is an electron attractive group selected from the group consisting of $CF_3$, CN, fluorine, $COSO_3H$, $CF_3SO_3$, and $NO_2$; and
$R_3$ is linear or branched alkyl having 1 to 10 carbon atoms, linear or branched alkoxyalkyl having 2 to 10 carbon atoms, aliphatic alcohol having 1 to 10 carbon atoms, or cycloalkyl having 3 to 6 carbon atoms;
or a pharmaceutically acceptable salt thereof.

9. The method according to claim 8, wherein $R_2$ is $CF_3$ or CN.

10. The method according to claim 8, wherein $R_3$ is linear or branched alkyl having 1 to 6 carbon atoms, linear or branched alkoxy having 2 to 6 carbon atoms, aliphatic alcohol having 1 to 6 carbon atoms, or cycloalkyl having 3 to 6 carbon atoms.

11. The method according to claim 8, wherein the pharmaceutically acceptable salt of the compound of formula (I) is a hydrochloride or hydrobromide salt.

12. A method of treating asthma or bronchitis in a subject, comprising:
administering to the subject a pharmaceutically effective amount of a pharmaceutical composition comprising a compound of formula (I)

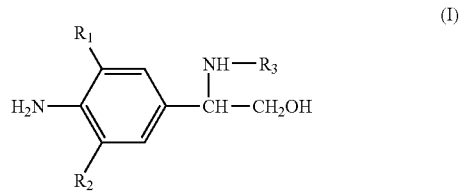

wherein:
$R_1$ is H, chlorine, bromine, iodine, or cyano;
$R_2$ is an electron attractive group selected from the group consisting of $CF_3$, CN, fluorine, $COSO_3H$, $CF_3SO_3$, and $NO_2$; and
$R_3$ is linear or branched alkyl having 1 to 10 carbon atoms, linear or branched alkoxyalkyl having 2 to 10 carbon atoms, aliphatic alcohol having 1 to 10 carbon atoms, or cycloalkyl having 3 to 6 carbon atoms;
or a pharmaceutically acceptable salt thereof.

13. The method according to claim 12, wherein $R_2$ is $CF_3$ or CN.

14. The method according to claim 12, wherein $R_3$ is linear or branched alkyl having 1 to 6 carbon atoms, linear or branched alkoxy having 2 to 6 carbon atoms, aliphatic alcohol having 1 to 6 carbon atoms, or cycloalkyl having 3 to 6 carbon atoms.

15. The method according to claim 12, wherein the pharmaceutically acceptable salt of the compound of formula (I) is a hydrochloride or hydrobromide salt.

16. The method according to claim 12, wherein the compound or its pharmaceutically acceptable salt is administered orally or paraterally.

17. The method according to claim 12, wherein the compound or its pharmaceutically acceptable salt is administered via inhalation.

18. The method according to claim 12, wherein the compound or its pharmaceutically acceptable salt is administered to a human subject at a dose of 50 μg-10 mg/day.

* * * * *

UNITED STATES PATENT AND TRADEMARK OFFICE
CERTIFICATE OF CORRECTION

| | |
|---|---|
| PATENT NO. | : 7,098,364 B2 |
| APPLICATION NO. | : 10/491028 |
| DATED | : August 16, 2004 |
| INVENTOR(S) | : Maosheng Cheng et al. |

It is certified that error appears in the above-identified patent and that said Letters Patent is hereby corrected as shown below:

On Title Page Item (75), Please delete "Lie" and replace with --Lei--.

On Title Page Item (75), Please delete "Zhiging" and replace with --Zinqing--.

On Title Page Item (87), Please delete "November 12, 2003" and replace with --November 13, 2006--.

Signed and Sealed this

Twenty-third Day of January, 2007

JON W. DUDAS
*Director of the United States Patent and Trademark Office*

UNITED STATES PATENT AND TRADEMARK OFFICE
CERTIFICATE OF CORRECTION

PATENT NO.         : 7,098,364 B2
APPLICATION NO. : 10/491028
DATED              : August 29, 2006
INVENTOR(S)       : Maosheng Cheng et al.

It is certified that error appears in the above-identified patent and that said Letters Patent is hereby corrected as shown below:

On Title Page Item (75), Please delete "Lie" and replace with --Lei--.

On Title Page Item (75), Please delete "Zhiging" and replace with --Zinqing--.

On Title Page Item (87), Please delete "November 12, 2003" and replace with --November 13, 2006--.

This certificate supersedes Certificate of Correction issued January 23, 2007.

Signed and Sealed this

Twentieth Day of February, 2007

JON W. DUDAS
*Director of the United States Patent and Trademark Office*